United States Patent [19]

Knifton

[11] 4,042,530
[45] Aug. 16, 1977

[54] OXYCHLORINATION SOURCES FOR REGENERATING DISPERSIONS OF LIGAND-STABILIZED, PALLADIUM (II) HALIDE COMPLEXES USED AS CARBONYLATION CATALYSTS

[75] Inventor: John F. Knifton, Poughquag, N.Y.

[73] Assignee: Texaco Inc., New York, N.Y.

[21] Appl. No.: 636,238

[22] Filed: Nov. 28, 1975

Related U.S. Application Data

[63] Continuation-in-part of Ser. No. 581,320, May 27, 1975.

[51] Int. Cl.² .................. B01J 31/40; B01J 27/32; C07C 51/00; C11C 3/02
[52] U.S. Cl. .................... 252/415; 252/414; 260/410.9 R; 260/429 R; 260/429.7; 260/468 M; 260/497 R; 260/514 M; 260/515 R; 260/533 A
[58] Field of Search .......... 252/414, 415, 416, 429 R; 260/410.9 R, 413, 533 A

[56] References Cited

U.S. PATENT DOCUMENTS 3,968,133   7/1976   Knifton .................. 260/410.9 R Primary Examiner—Winston A. Douglas
Assistant Examiner—P. E. Konopka
Attorney, Agent, or Firm—Thomas H. Whaley; Carl G. Ries; Bernard Marlowe

[57] ABSTRACT

This invention concerns process for the regeneration of carbonylation catalysts consisting of dispersions of ligand-stabilized palladium(II) halide complexes in quaternary ammonium, phosphonium and arsonium salts of trihalostannate(II) and trihalogermanate(II). The regeneration agents are those which are generically classified as oxychlorinating agents.

1 Claim, No Drawings

OXYCHLORINATION SOURCES FOR REGENERATING DISPERSIONS OF LIGAND-STABILIZED, PALLADIUM (II) HALIDE COMPLEXES USED AS CARBONYLATION CATALYSTS

This invention is a continuation-in-part of Ser. No. 581,320 filed in the United States Patent Office on May 27, 1975.

STATEMENT OF THE INVENTION

This invention pertains to the art of regenerating spent palladium carbonylation catalysts useful for the carbonylation of olefins.

More particularly, this invention concerns the regeneration of certain carbonylation catalysts consisting of dispersions of ligand-stabilized palladium(II) halide complexes in quaternary ammonium, phosphonium and arsonium salts of trihalostannate(II) and trihalogermanate(II) using oxychlorination agents as the regeneration means.

BACKGROUND OF THE INVENTION

This invention concerns a process for regenerating certain palladium catalysts used in the carbonylation of olefins. Carbonylation refers here to the reaction of olefins with carbon monoxide and active-hydrogen-containing compounds selected from the group consisting of an alkanol or water. Suitable alkanols (ROH) include primary and secondary alcohols, glycols and polyols.

Oxychlorination as used throughout this application refers to processes wherein hydrogen chloride plus oxygen or air are used to regenerate a spent catalyst used for carbonylation of olefins.

The preparation of the fatty acids or fatty acid esters using metal carbonyls or carbonyl precursors to catalyze the carbonylation of olefins is old in the literature, originally involving Reppe and his coworkers and contemporaries. Reviews by C.W. Bird [Chem.Rev. 62, 283 (1962)] document this work. Unfortunately, many of these carbonyl or carbonyl-type catalysts have the disadvantages of inherent toxicity, they require stringent reaction conditions which in turn lead to competing side reactions such as olefin isomerization, polymerization and reduction, and they exhibit poor selectivity to the desired linear acid ester.

Recently, more acceptable homogeneous catalyst systems have been developed which offer substantially improved selectivity in converting olefins to primarily linear fatty acids or linear fatty esters, in good yield, under moderate reaction conditions of temperature and pressure.

As is usually the case, after much more extensive usage, certain drawbacks in the catalysts have become more evident. These include difficulty in maintaining high conversions, high selectivities and high yields after recycling the catalyst several times. These problems are due to catalyst degradation as well as catalyst decomposition, mechanical losses and further catalyst decomposition during the separation of the products from the homogeneous catalysts and the inert solvents of the reaction mixture. Thermal instability of the catalyst is particularly troublesome in the recovery and working-up of certain ligand-stabilized homogeneous palladium catalyst reaction mixtures.

In order to avoid or minimize these problems, the use of molten quaternary ammonium, phosphonium and arsonium salts of trihalostannate(II) or trihalogermanate (II) as both solvent and part of the catalytic entity has been disclosed, particularly in the two United States patents of G.W. Parshall, U.S. Pat. Nos. 3,657,368 and 3,565,823, which are known art, as well as in applicant's more recently filed one parent case listed above. In the parent application certain criteria are discussed which are required in order to establish an advantageous catalytic carbonylation process. They are:

1. A simple and efficient means of separating catalysts from the products,
2. The ability to recycle the catalyst without its substantial deactivation or loss of selectivity. This is particularly important since the palladium catalysts are thermally sensitive, and
3. In addition, to minimize capital costs, it is desirable that the process be able to operate at high concentrations of catalyst in the feed stream.

In the cited United States Patents Nos. 3,657,368 and 3,565,823 are also disclosed two illustrative procedures for isolating ester or acid products, such as are produced by olefin carbonylation, in high purity, from palladium catalysts consisting of dispersions of ligand-stabilized palladium(II) halide in quaternary ammonium, phosphonium and arsonium salts of trihalostannate(II) and trihalogermanate(II). Briefly, one procedures involves solvent extraction, the other, vacuum distillation.

Also disclosed in applications Ser. Nos. 581,320 and 581,395 are two illustrative procedures for regenerating the same palladium catalysts after multiple cycling. These two different procedures involve treatment of the spent catalyst with chlorine or mixed mineral acids. Each procedure is a process improvement which provides a useful means of extending the life of the palladium catalyst, and thereby it allows the development of a more efficient carbonylation process.

DESCRIPTION OF THE INVENTION

The critical aspect of this application is the claimed process for restoring the activity of the above mentioned spent catalyst dispersions of ligand-stabilized palladium(II) halide salts in quaternary ammonium, phosphonium and arsonium salts of trihalostannate(II) and trihalogermanate(II) by treatment with oxychlorination agents. Suitable oxychlorination agents consist of hydrogen chloride in combination with a source of oxygen selected from the group consisting of oxygen and air.

After separation of the desired products of the carbonylation process from the spent palladium catalyst by either distillation or extractive means, said catalyst may be regenerated by the following general procedure:

a. The spent catalyst is suspended in a suitable inert organic solvent and contacted with a mixed gas stream consisting of hydrogen chloride in combination with oxygen or air for 0.1 to 48 hours at 20° to 200° C.

b. Excess liquid is removed by distillation under reduced pressure.

c. Additional stabilizing ligand, such as triphenylphosphine, is added to the catalyst in the mole ratio of 1–10 mole ligand per mole Pd.

Generally, speaking, the spent palladium catalyst may be contacted with the oxychlorinating agent by any convenient means. One convenient mode is to hook-up a flow meter into the regeneration system and to permit the hydrogen chloride plus air or oxygen to bubble through the suspension of spent catalyst in inert solvent for a period of 0.1 to 48 hours, preferably between 2 and 12 hours, at a rate of between 1 and 500 ml per minute. The volume ratio of hydrogen chloride to oxygen, or air, may vary from 10:1 to 1:10. Regeneration is considered to have occurred when a sample of oxychlorinated catalyst delivers a selectivity to the desired linear fatty (carboxylic) acid or ester of between 70 and 95%, and a yield of total ester between 20 and 95 mole %.

Oxychlorination with hydrogen chloride plus oxygen is exemplified in Example 1, described infra. Example 2 discloses the use of hydrogen chloride plus air as the regenerating agent.

Suitable inert solvents for the oxychlorination step may be selected from the group consisting of chlorinated aliphatics, such as carbon tetrachloride, chloroform, dichloromethane, dichloroethane, and chlorohexane, aromatic solvents such as benzene, toluene and xylenes, and chlorinated aromatics like o-dichlorobenzene, chlorobenzene and chlorotoluene, and mixtures thereof. A further possible class of suitable solvents for the oxychlorination step are fatty (carboxylic) acid esters, particularly those esters generated by the palladium catalyst carbonylation of the olefin, alkanol feed stocks during prior carbonylation cycles.

Regeneration of palladium carbonylation catalysts via oxychlorination is exemplified infra in Examples 1 and 2 for the melt complex $[(C_2H_5)_4N][SnCl_3]\text{-}PdCl_2[((C_6H_5)_3]_2$, but other palladium carbonylation catalysts may also be regenerated by this technique. These catalyst generally consist of ligand-stabilized palladium(II) halide complexes dispersed in quaternary ammonium, phosphonium and arsonium salts of trihalostannate(II) and trihalogermanate (II). They are illustrated, but not limited by, the carbonylation catalysts described in Examples 3 to 9.

Other substrate mixtures beyond the 1-octene, ethanol used in Examples 1 and 2 may also be carbonylated by the regenerated palladium carbonylation catalysts. Some typical examples are given in Examples 10-15, described infra. Generally, for the carbonylation of α-olefins, as exemplified in Equation 1, $R_1$ and $R_2$, individually, may be hydrogen, alkyl up to 12 carbon atoms, alkenyl up to 12 carbon atoms, or aryl up to 12 carbon atoms, or mixed alkyaryl or arylalkyl groups. Suitable Alkanols (ROH)

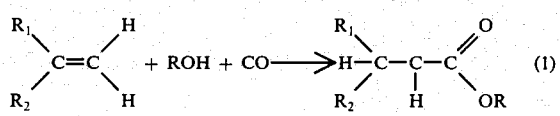 (1)

include primary and secondary alcohols of up to 12 carbon atoms, phenols, substituted alcohols and polyols. The major products of the carbonylation reaction are fatty (carboxylic) acids and their esters.

EXAMPLE 1

PREPARATION OF ETHYL NONANOATE WITH RECOVERY BY DISTILLATION AND REGENERATION OF THE SPENT CATALYST BY OXYCHLORINATION WITH HCl PLUS OXYGEN

A. Isolation of Product.

To a degassed sample of 1-octene (0.5 mole) and ethanol (0.5 mole) contained in a glass lined reactor equipped for pressurizing, heating, cooling and means of agitation, is added the following reactants under a nitrogen purge, tetraethylammonium trichlorostannate(II) (8.0 mole) and bis(triphenylphosphine) palladium(II) chloride (8.0 mmole). The mixture is purged with carbon monoxide and heated to 80° C under 1500 psig of carbon monoxide. The carbonylation reaction is terminated after 6-8 hours by cooling and venting, and the liquid product (108 ml) recovered from the solid catalyst by filtration. Unreacted octenes and ethanol are removed by distillation under reduced pressure (5 cm Hg) and the residual liquid subjected to fractional distillation in vacuo. Ethyl nononoate products are recovered in up to 72 mole % yield (>99% purity) as distillate fraction having a boiling point of 58°-62° C at 2 mm Hg pressure. The residual palladium chloride catalyst, $[(C_2H_5)_4N][SnCl_3]\text{-}PdCl_2]P[(C_6H_5)_3]_2$, is recharged to the reactor with additional fresh 1-octene (0.5 mole) and ethanol (0.5 mole) and the carbonylation reaction is repeated as described above. Ethyl nonanoates are recovered by distillation.

B. Regeneration of Catalyst.

After being used for four carbonylation cycles the palladium catalyst is treated with 100 ml of pentachloroethane and the mixture heated to reflux (120°-130° C) in a stream of hydrogen chloride plus oxygen (1 to 1 volume ratio; flow rate 50-100 ml./min) for 3-5 hours. Excess solvent is removed by distillation under reduced pressure (5 cm Hg) and the recovered catalyst is dried in vacuo. Triphenylphosphine (4.19 grams, 16 mmole) is added to the dried solids (above) and the mixture recharged to the pressure reactor with fresh feed (1-octene plus ethanol, 0.5 mole each). Carbonylation and ethyl nonanoate recovery is as described above. Oxychlorination is repeated after the 9th and 13th cycle. The total yield of ethyl nonanoates after 16 cycles is 404 mole per g./atom of Pd charge, the maximum yield certainly exceeds 404 moles/g. atoms of Pd charged.

TABLE I

CARBONYLATION CATALYST LIFE STUDY[a] WITH REGENERATION VIA OXYCHLORINATION WITH HCl PLUS OXYGEN[d]

| CYCLE | PROCEDURE | ETHYL C$_9$ ESTER LINEARITY (%) | YIELD(MOLE %)[a] | LIQUID YIELD(%) | ISOLATED ESTER PURITY(%)[f] |
|---|---|---|---|---|---|
| I | Fresh Melt Catalyst | 67.1 | 99 | 97 | 99 |
| II | Recycle | 85.6 | 82 | 98 | 99 |
| III | " | 91.5 | 51 | 102 | 99 |
| IV | " | 91.5 | 16 | 96 | 99 |
| V | HCl/O$_2$[b] + PPh$_3$ | 91.9 | 30 | 85 | 99 |
| VI | Recycle | 92.2 | 82 | 86 | 99 |
| VII | " | 89.2 | 86 | 85 | 99 |
| VIII | " | 88.9 | 22 | 97 | 99 |
| IX | " | 88.4 | 5.3 | 93 | 96 |
| X | HCl/O$_2$[b] + PPh$_3$ | 85.0 | 1.8 | 85 | 97 |
| XI | Recycle | 79.1 | 70 | 89 | 99 |
| XII | " | 83.2 | 44 | 98 | 99 |
| XIII | " | 84.0 | 3.5 | 96 | 94 |

TABLE I-continued
CARBONYLATION CATALYST LIFE STUDY[a] WITH REGENERATION VIA OXYCHLORINATION WITH HCl PLUS OXYGEN[d]

| CYCLE | PROCEDURE | ETHYL C₉ ESTER LINEARITY (%) | YIELD(MOLE %)[a] | LIQUID YIELD(%) | ISOLATED ESTER PURITY(%)[f] |
|---|---|---|---|---|---|
| XIV | HCl/O₂[c] + PPh₃ | 88.0 | 20 | 93 | 97 |
| XV | Recycle | 86.8 | 28 | 93 | 99 |
| XVI | " | 86.5 | 0.9 | 96 | 92 |

[a]Carbonylation Conditions: Initial [1-octene]/[Pd]=63:1; 85° C; 1500 psig CO.
[b]Using pentachloroethane as solvent, oxychlorination temperature 120–130° C.
[c]Using carbon tetrachloride as solvent; oxychlorination temperature 70–72° C.
[d]Oxychlorination using HCl/O₂ in 1:1(v/v) ratio, flow rate 50–100 ml/min.
[e]Estimated by GLPC analysis of crude product, based on 1-octene charged.
[f]Estimated by GLPC analysis of isolated (distilled) product.

EXAMPLE 2

PREPARATION OF ETHYL NONANOATE WITH RECOVERY BY DISTILLATION AND REGENERATION OF THE SPENT CATALYST BY OXYCHLORINATION WITH HCl PLUS AIR

To a degassed sample of 1-octene (0.4 mole) and ethanol (0.4 mole) contained in a glass lined reactor equipped for pressurizing, heating, cooling and means of agitation, is added the following under a nitrogen purge, tetraethylammonium trichlorostannate(II) (50 mmole) and bis(triphenylphosphine) palladium(II) chloride (5.0 mmole). The mixture is purged with carbon monoxide and heated to 80° C for 8 hours under 1500 psig of carbon monoxide. Ethyl nonanoate esters are isolated by distillation as described in Example 1. The residual palladium catalyst is recharged to the reactor with additional fresh 1-octene (0.4 mole) and ethanol (0.4 mole) and the carbonylation reaction repeated as described.

After four carbonylation cycles the palladium catalyst is treated with 100 ml of carbon tetrachloride and the mixture heated to reflux (75°–78° C) in a stream of hydrogen chloride plus air (1 to 3 volume ratio, flow rate 200 ml/min) for 6 hours. Excess solvent is removed by distillation under reduced pressure (5 cm Hg) and the recovered catalyst is dried in vacuo. Triphenylphosphine (2.62 gm, 10 mmole) is added to the dried solids and the mixture recharged to the pressure reactor with fresh feed (1-octene plus ethanol, 0.4 mole each). Again carbonylation and ethyl nonanoate recovery is as described infra.

Oxychlorination is repeated after the 7th cycle using product ethyl nonanoates as the inert organic medium. The total yield of ethyl nonanoates after 10 cycles is 260 mole per gm atom of Pd charge, the maximum yield of ester certainly exceeds this figure.

TABLE II
CARBONYLATION CATALYST LIFE STUDY[a] WITH REGENERATION VIA OXYCHLORINATION WITH HCl PLUS AIR[b]

| CYCLE | PROCEDURE | ETHYL C₉ ESTER LINEARITY(%)[e] | YIELD(MOLE%)[f] | LIQUID YIELD | ISOLATED ESTER PURITY(%)[e] |
|---|---|---|---|---|---|
| I | Fresh Melt Catalyst | 88.2 | 78 | 92 | 99 |
| II | Recycle | 88.0 | 45 | 106 | 99 |
| III | " | 89.1 | 7.7 | 98 | 99 |
| IV | " | 86.2 | 5 | 108 | 90 |
| V | HCl/Air[c] + PPh₃ | 83.5 | 77 | 85 | 99 |
| VI | Recycle | 83.2 | 54 | 99 | 99 |
| VII | " | 82.0 | 9.9 | 94 | 99 |
| VIII | HCl/Air[d] + PPh₃ | 90.5 | 13 | 94 | 99 |
| IX | Recycle | 88.5 | 31 | 97 | 99 |
| X | " | 88.6 | 3.9 | 97 | 99 |

[a]Carbonylaton Conditions: Initial [1-octene]/[pd]=80:1; 85° C; 1500 psig CO.
[b]Oxychlorination using HCl/Air in 1:3(v/v) ratio,
[c]With carbon tetrachloride as solvent, oxychlorination temperature 75–78° C
[d]With ethyl nonanoates as solvent, oxychlorination temperature 120–130° C
[e]Estimated by GLPC analysis of isolated(distilled) products
[f]Estimated by GLPC analysis of crude liquid product, based on 1-octene charged.

EXAMPLES 3–9
PALLADIUM CATALYST REGENERATION EFFECT OF CATALYST COMPOSITION

In these examples the carbonylation of 1-octene, ethanol samples and regeneration of palladium catalyst are carried out in accordance with the procedure outlined in Example 1, but in the present of various other ligand-stabilized palladium(II) halide complexes dispersed in quaternary ammonium, phosphonium and arsonium salts of trihalostannate(II) and trihalogermanate(II). The following catalyst compositions showed satisfactory performance for ethyl nonanoate synthesis over 8 cycles:

10[(C₂H₅)₄N][SnCl₃]-PdCl₂[P(p-CH₃.C₆H₄)₃]₂
5[ClCH₂(C₆H₅)₃P][SnCl₃]-PdCl₂[P(C₆H₅)₃]₂
10[(n-C₄H₉)₄N][SnCl₃]-PdCl₂[P(C₆H₅)₃]₂
10[(C₆H₅)₄As][SnCl₃]-PdCl₂[P(C₆H₅)₃]₂
5[(C₂H₅)₄N][GeCl₃]-PdCl₂[P(C₆H₅)₃]₂
10[(C₂H₅)₄N][SnCl₃]-PdCl₂[P(p-CH₃O.C₆H₄)₃]₂
5[(C₇H₁₅)₄N][GeCl₃]-PdCl₂[As(C₆H₅)₃]₂

EXAMPLES 10–15
PALLADIUM CATALYST REGENERATION EFFECT OF CHANGES IN REACTANTS

In these examples the carbonylation of samples of equimolar α-olefin-alkanol mixtures are carried out in accordance with the procedure outline in Example 1, using the same dispersions of palladium complex in quaternary salt, viz.

10 [(C$_2$H$_5$)$_4$N][SnCl$_3$]-PdCl$_2$[P(C$_6$H$_5$)$_3$]$_2$

The following olefin-alkanol mixtures gave good yields of the corresponding esters over 8 catalyst cycles.

| Propylene | — | 1-decanol |
| 1-Hexene | — | iso-propanol |
| 1-Decene | — | 2-chlorethanol |
| 1-Tetradecene | — | methanol |
| 1-Octene | — | 2-ethylhexanol |
| 1-Octene | — | phenol |

As the previous data and comments have indicated, the use of oxychlorination of catalyst regeneration of this invention is both novel and useful. They may be applied to catalyst consisting of dispersions of ligand-stabilized palladium salts in quaternary ammonium, phosphonium and arsonium salts of trihalostannate(II) or trihalogermanate(II) useful in the catalyst carbonylation of olefins.

Further, the invention processes are flexible in permitting changes and moxifications to be made without departing from the inventive process.

However, the metes and bounds of this invention can best be gleaned by reading the claims that follow, in conjunction with the rest of the specification.

What is claimed is:

1. A process for regenerating spent carbonylation catalyst of ligand-stabilized palladium(II) halide complexes in quaternary ammonium, phosphonium and arsonium salts of trihalostannate(II) or trihalogermanate(II), the spent catalyst being obtained from the carbonylation of olefins, wherein said ligand stabilized catalysts are selected from the group consisting of:

[(C$_2$H$_5$)$_4$N][SnCl$_3$]-PdCl$_2$[P(C$_6$H$_5$)$_3$]$_2$
[(C$_2$H$_5$)$_4$N][SnCl$_3$]-PdCl$_2$[P(p-CH$_3$.C$_6$H$_4$)$_3$]$_2$
[ClCH$_2$(C$_6$H$_5$)$_3$P][SnCl$_3$]-PdCl$_2$[P(C$_6$H$_5$)$_3$]$_2$
[(n.C$_4$H$_9$)N][SnCl$_3$]-PdCk$_2$[P(C$_6$H$_5$)$_3$]$_2$
[(C$_6$H$_5$)$_4$As][SnCl$_3$]-PdCl$_2$[P(C$_6$H$_5$)$_3$]$_2$
[(C$_2$H$_5$)$_4$N][GeCl$_3$]-PdCl$_2$[P(C$_6$H$_5$)$_3$]$_2$
[(C$_2$H$_5$)$_4$N][SnCl$_3$]-PdCl$_2$[P(p-CH$_3$I.C$_6$H$_4$)$_3$]$_2$, and
[(C$_7$H$_{15}$)$_4$N][GeCl$_3$]-PdCl$_2$[As(C$_6$H$_5$)$_3$]$_2$, by the a. mixing said spent palladium carbonylation catalyst with inert solvent selected from the group consisting of chlorinated aliphatics, chlorinated aromatics, aromatics and carboxylic acid esters to form a reaction mixture, b. heating said reaction mixture at temperatures ranging from 20° to 200° C for a time of 0.1 to 48 hours, in a stream of hydrogen chloride plus a source of oxygen selected from the group consisting of oxygen and air, said volume ratio of hydrogen chloride ratio to oxygen or varying from 10:1 to 1:10, c. removing excess solvent under reduced pressure until a dried palladium catalyst is obtained, and d. adding additional stabilizing ligand to the dried catalyst wherein the stabilizing ligand is selected from the group consisting of tri henylphosphine, triphenylarsine, tri-p-tolylphosphine, and tri-p-methoxyphenylphosphine, said mole ratio of ligand added per gram atom of palladium varies from 1 to 10 moles of ligand per gram atom of palladium, until said spent ligand catalyst is regenerated.

* * * * *